(12) United States Patent
Miyamura et al.

(10) Patent No.: US 10,241,068 B2
(45) Date of Patent: Mar. 26, 2019

(54) REFERENCE ELECTRODE

(71) Applicant: HORIBA, Ltd., Kyoto-shi, Kyoto (JP)

(72) Inventors: Kazuhiro Miyamura, Kyoto (JP); Hiroki Minowa, Kyoto (JP); Yoko Nakai, Kyoto (JP)

(73) Assignee: HORIBA, Ltd., Kyoto-shi, Kyoto (JP)

( * ) Notice: Subject to any disclaimer, the term of this patent is extended or adjusted under 35 U.S.C. 154(b) by 146 days.

(21) Appl. No.: 15/362,306

(22) Filed: Nov. 28, 2016

(65) Prior Publication Data

US 2017/0168004 A1    Jun. 15, 2017

(30) Foreign Application Priority Data

Dec. 14, 2015 (JP) ................................ 2015-243583

(51) Int. Cl.
*G01N 27/31* (2006.01)
*G01N 27/30* (2006.01)

(52) U.S. Cl.
CPC ................................ *G01N 27/301* (2013.01)

(58) Field of Classification Search
CPC ............................ G01N 27/30; G01N 27/301
See application file for complete search history.

(56) References Cited

U.S. PATENT DOCUMENTS

| 9,140,660 B2 * | 9/2015 | Yang | G01N 27/301 |
| 2017/0038329 A1 * | 2/2017 | Yang | G01N 27/301 |
| 2018/0003664 A1 * | 1/2018 | Miyamura | G01N 27/301 |
| 2018/0011045 A1 * | 1/2018 | Miyamura | G01N 27/301 |

FOREIGN PATENT DOCUMENTS

JP    2005172539 A    6/2005

\* cited by examiner

*Primary Examiner* — Alexander W Keeling
(74) *Attorney, Agent, or Firm* — Alleman Hall Creasman & Tuttle LLP

(57) ABSTRACT

In order to provide a reference electrode capable of suppressing an error in a measured value even when refilling an internal solution during sample measurement, a reference electrode including: a casing adapted to store the internal solution in an internal space; and an internal electrode that rises from the bottom surface of the internal space and is immersed in the internal solution further includes: a surrounding wall that rises from the bottom surface so as to surround the side circumferential surface of the internal electrode; and an inlet port that is for refilling the internal solution in the casing. In addition, in the reference electrode, the surrounding wall is adapted such that a fore end surface thereof is opened and the height thereof is higher than the height of the internal electrode, and the inlet port is adapted to be opened toward a space outside the surrounding wall.

3 Claims, 3 Drawing Sheets

REFERENCE ELECTRODE

TECHNICAL FIELD

The present invention relates to a reference electrode used for, for example, a pH measuring instrument.

BACKGROUND ART

When refiling a reference electrode with an internal solution, an error occurs in the output value of a measuring instrument. The reason for this is as follows.

A silver/silver chloride electrode used as the reference electrode is one in which a silver chloride layer is formed by such as electrodeposition around a rod-shaped or plate-shaped core material made of silver.

The reference potential of the silver/silver chloride electrode is known to depend on the concentration of chloride ions in the internal solution. However, when silver ions are eluted through cracks and/or the like present in the silver chloride layer, the surrounding silver chloride is reduced to release chloride ions into the internal solution, and therefore the chloride ion concentration in the internal solution is slightly changed to change the reference potential of the silver/silver chloride electrode.

The change in the reference potential is stabilized when the silver ions are saturated in the internal solution. However, when refilling a new internal solution, the elution of silver ions again occurs from an internal electrode to change the reference potential, and as a result, every time the internal solution is refilled, an error occurs in the measured value of the measuring instrument.

In the past, when measuring a sample that is stored in a container and has a constant characteristic value, an internal solution has been refilled before the measurement, and the sample has been measured after the output value of a measuring instrument was stabilized.

However, when refilling an internal solution during sample measurement, in particular, when continuously measuring a sample whose measured value keeps changing or samples supplied one after another, an error in a measured value due to refilling the internal solution becomes a big problem.

CITATION LIST

Patent Literature

Patent Literature 1: Japanese Unexamined Patent Publication JP-A 2005-172539

SUMMARY OF INVENTION

Technical Problem

The present invention is made in consideration of the above problem and intends to provide a reference electrode capable of, even when refilling an internal solution during sample measurement, suppressing an error in a measured value.

Solution to Problem

That is, the reference electrode according to the present invention is a reference electrode including: a casing adapted to store an internal solution (internal liquid) in an internal space; and an internal electrode that rises from the bottom surface of the internal space and is arranged so as to be immersed in the internal solution, and the reference electrode further includes: a surrounding wall that rises from the bottom surface so as to surround the side circumferential surface of the internal electrode; and an inlet port for refilling the internal solution in the casing. In addition, the surrounding wall is one of which the fore end surface is opened and the height is higher than the height of the internal electrode, and the inlet port is opened toward a space outside the surrounding wall.

In such a reference electrode, when refilling the internal solution, the internal solution fed from the inlet port is first refilled in outside of the surrounding wall and thereby prevented from immediately mixing with the internal solution containing silver ions eluted from the internal electrode inside the surrounding wall, and therefore an error in a measured value occurring when refilling the internal solution can be suppressed.

In the reference electrode in which the inlet port is one opened toward the space between the outer circumferential surface of the surrounding wall and the inner surface of the casing, even when the internal solution, which is refilled from the inlet port and new, is refilled from outside the surrounding wall, the height of the surrounding wall is in a position higher than the height of the inlet port, and is therefore required to get over the surrounding wall in order to mix with the internal solution inside the surrounding wall. Accordingly, since the new internal solution is more unlikely to mix with the internal solution inside the surrounding wall, the error in a measured value occurring when refilling the internal solution can be more effectively suppressed.

Specific embodiments adapted to make the effect of the present invention particularly remarkable include the reference electrode including an internal solution refilling mechanism, in which the internal solution refilling mechanism is one that continuously or intermittently refills the internal solution during sample measurement.

In the reference electrode in which the internal electrode is a silver/silver chloride electrode with silver as a core material and silver chloride coated around the core material and which further includes a filling material that is filled in the space formed between the side circumferential surface of the internal electrode and the inner circumferential surface of the surrounding wall, the internal electrode can be protected by the filling material to suppress silver ions from being eluted into the internal solution, and therefore the error in a measured value occurring when refilling the internal solution can be further suppressed.

ADVANTAGEOUS EFFECTS OF INVENTION

In the reference electrode as described above, the internal solution fed from the inlet port when refilling the internal solution is first refilled in outside of the surrounding wall and thereby prevented from immediately mixing with the internal solution containing silver ions eluted from the internal electrode inside the surrounding wall, and therefore an error in a measured value occurring when refilling the internal solution can be suppressed

DESCRIPTION OF EMBODIMENTS

In the following, one embodiment of the present invention will be described with reference to drawings.

A reference electrode 22 according to the present embodiment is one used for a measuring instrument 100 that is connected to and incorporated in a semiconductor manufacturing apparatus in order to measure the pH of a measured liquid, such as a chemical liquid used in a semiconductor manufacturing process, such as a cleaning liquid, a Cu plating liquid, an etching liquid for fabricating wiring e.g., and a chemical liquid used for CMP (chemical mechanical polishing) e.g. in a wiring process.

Figure 1:
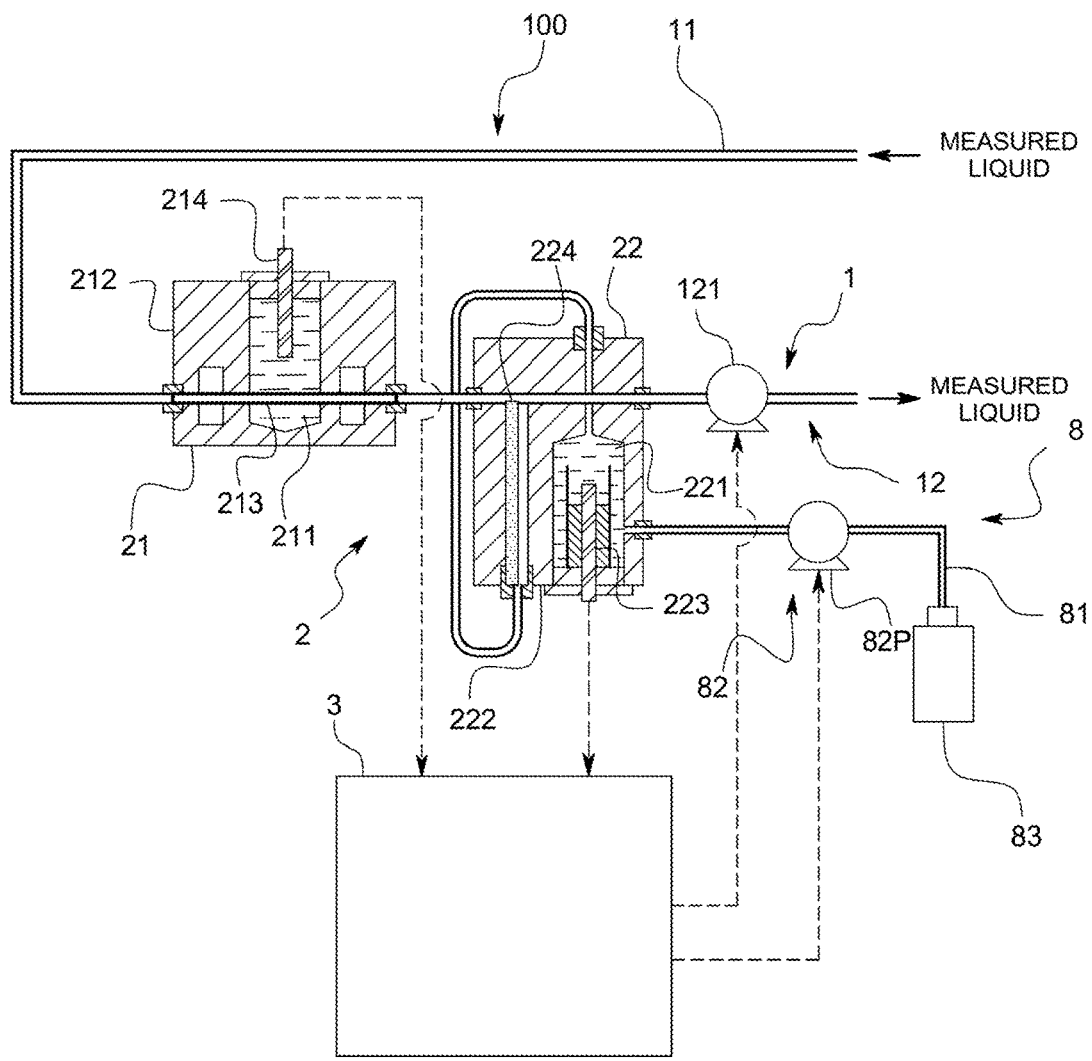
FIG. 1 is an overall schematic view of a measuring instrument according to one embodiment of the present invention.
Figure 3:
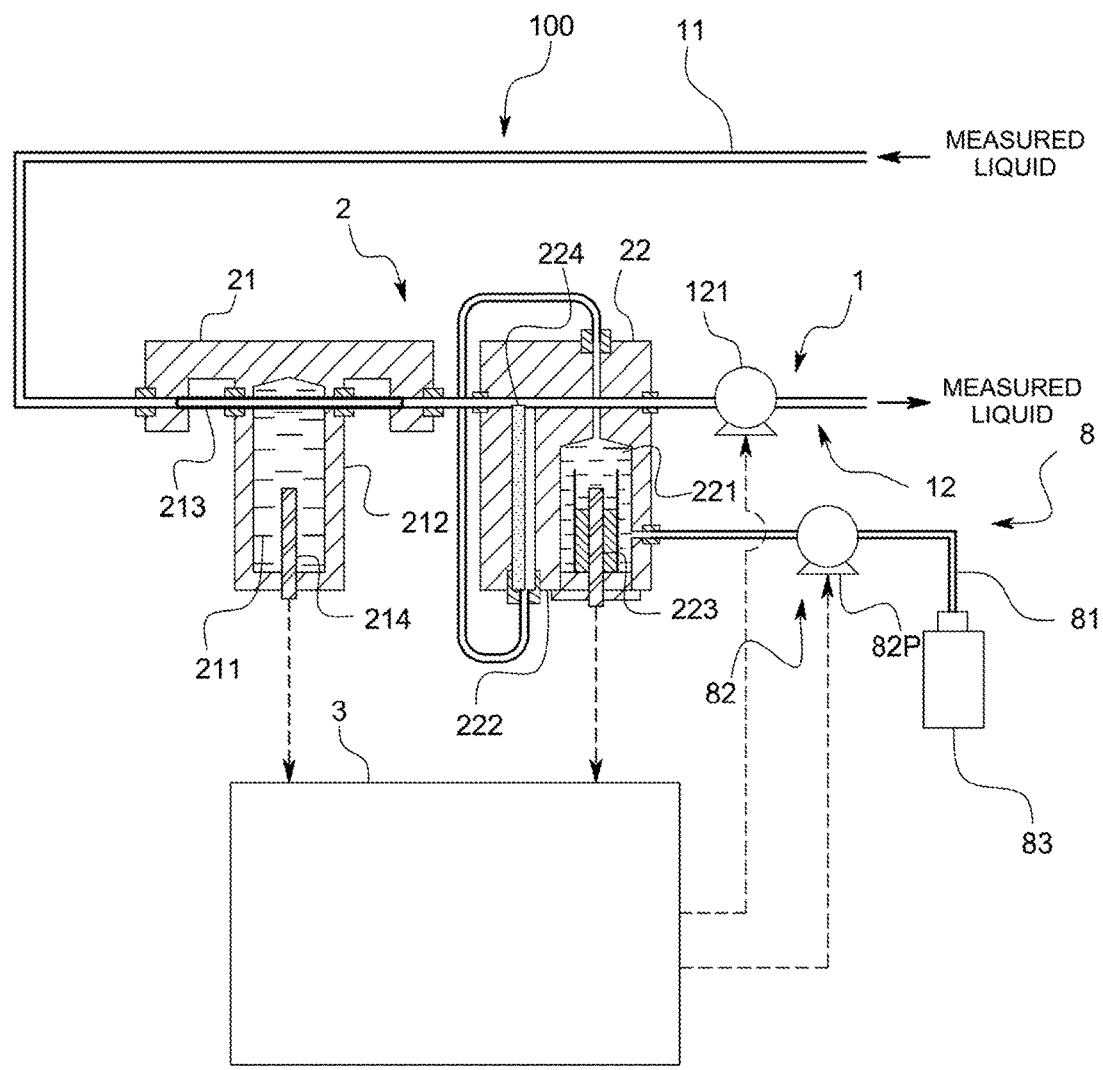
FIG. 3 is an overall schematic view of a measuring instrument according to another embodiment.

As illustrated in FIG. 1 or FIG. 3, the measuring instrument 100 is one that is connected to a main flow path (not illustrated) through which the measured liquid flows, and includes a sampling mechanism 1 adapted to sample part of the measured liquid and a pH meter 2 adapted to measure the pH of the sampled measured liquid.

The sampling mechanism 1 is one including: a sampling flow path 11 communicatively connecting to the main flow path; and a circulation control mechanism 12 adapted to control such as the introduction of the measured liquid as a measurement sample into the sampling flow path 11.

The sampling flow path 11 is a flow path through which the sampled measured liquid or a calibration liquid flows. In addition, the sampling flow path 11 is formed of a tubing member having corrosion resistance to the measured liquid and a very thin path forming a capillary shape.

The circulation control mechanism 12 is one including a sampling pump 121 provided in the sampling flow path 11 and a sampling control part adapted to control the action of the sampling pump 121.

In the present embodiment, the sampling control part is such that an information processing circuit 3 provided separately from the sampling pump 121 plays the role of the sampling control part. The information processing circuit 3 is one including some circuits such as: a digital circuit configured to include a CPU, memory, communication port, and the like; an analog circuit including a buffer, an amplifier, and the like; and AD and DA converters adapted to act as a bridge between the digital circuit and the analog circuit. In addition, the CPU and its peripheral devices cooperate in accordance with a predetermined program stored in the memory, and thereby the information processing circuit 3 fulfills a function as the sampling control part.

Further, it is configured to, when the sampling pump 121 operates in accordance with a command signal from the sampling control part, draw the part of the measured liquid flowing through the main flow path into the sampling flow path 11, and when the sampling pump 121 stops, stop sampling the measured liquid.

The pH meter 2 is one adapted to measure the pH on the basis of a so-called glass electrode method here, and includes a glass electrode 21, the reference electrode 22, and a pH calculation part adapted to calculate the pH on the basis of the potential difference between the respective electrodes 21 and 22.

As illustrated in FIG. 1, the glass electrode 21 is one that includes: a first body 212 that stores a first internal solution 211 inside; responsive glass that is provided to the first body 212; and a first internal electrode 214 that is immersed in the first internal solution 211.

The first body 212 is one that is formed of a material such as PVC (polyvinyl chloride), PP (polypropylene), PVDF (polyvinylidene fluoride), PTFE (polytetrafluoroethylene), or PFA (Perfluoroalkoxy alkane) and forms a hollow block body shape.

The first internal solution 211 is, for example, an aqueous solution of potassium chloride, ammonium nitrate, lithium acetate.

As well known, the responsive glass is one that interposes between the first internal solution 211 and the measured liquid as a measurement target and produces a potential due to the pH difference between the first internal solution 211 and the measured liquid. In the present embodiment, a tubular body 213 is formed of the responsive glass.

The tubular body 213 formed of the responsive glass is a very thin body that is made to penetrate so as to pass from one side surface of the first body 212 to the other side surface through a first internal space as an internal space of the first body 212 and forms a capillary shape similarly to the sampling flow path 11.

Note that the capillary shape refers to the shape of a tube of which the inside diameter is approximately 5 mm or less, preferably 3 mm or less, and the length is approximately five or more times the inside diameter.

The start edge of the tubular body 213 is connected to the sampling flow path 11, and adapted such that the operation of the sampling pump 121 allows the measured liquid to be introduced from the main flow path into the tubular body 213.

Thus, the outer surface of the tubular body 213 contacts with the first internal solution 211 filled in the first internal space, and in addition to this, the introduction of the measured liquid into the tubular body 213 allows the responsive glass (tubular body 213) to interpose between the first internal solution 211 and the measured liquid as the measurement target as described above.

Note that in the present embodiment, the whole of the tubular body 213 is formed of the responsive glass; however, only a part contacting with the first internal solution 211 may be formed of the responsive glass.

The first internal electrode 214 is one that, for example, is formed of silver/silver chloride and forms a rod shape or a long plate shape. Also, the first internal electrode 214 is attached so as to penetrate through a wall of the first body 212, and thereby part of the first internal electrode 214 is adapted to be immersed in the first internal solution 211.

Figure 2:
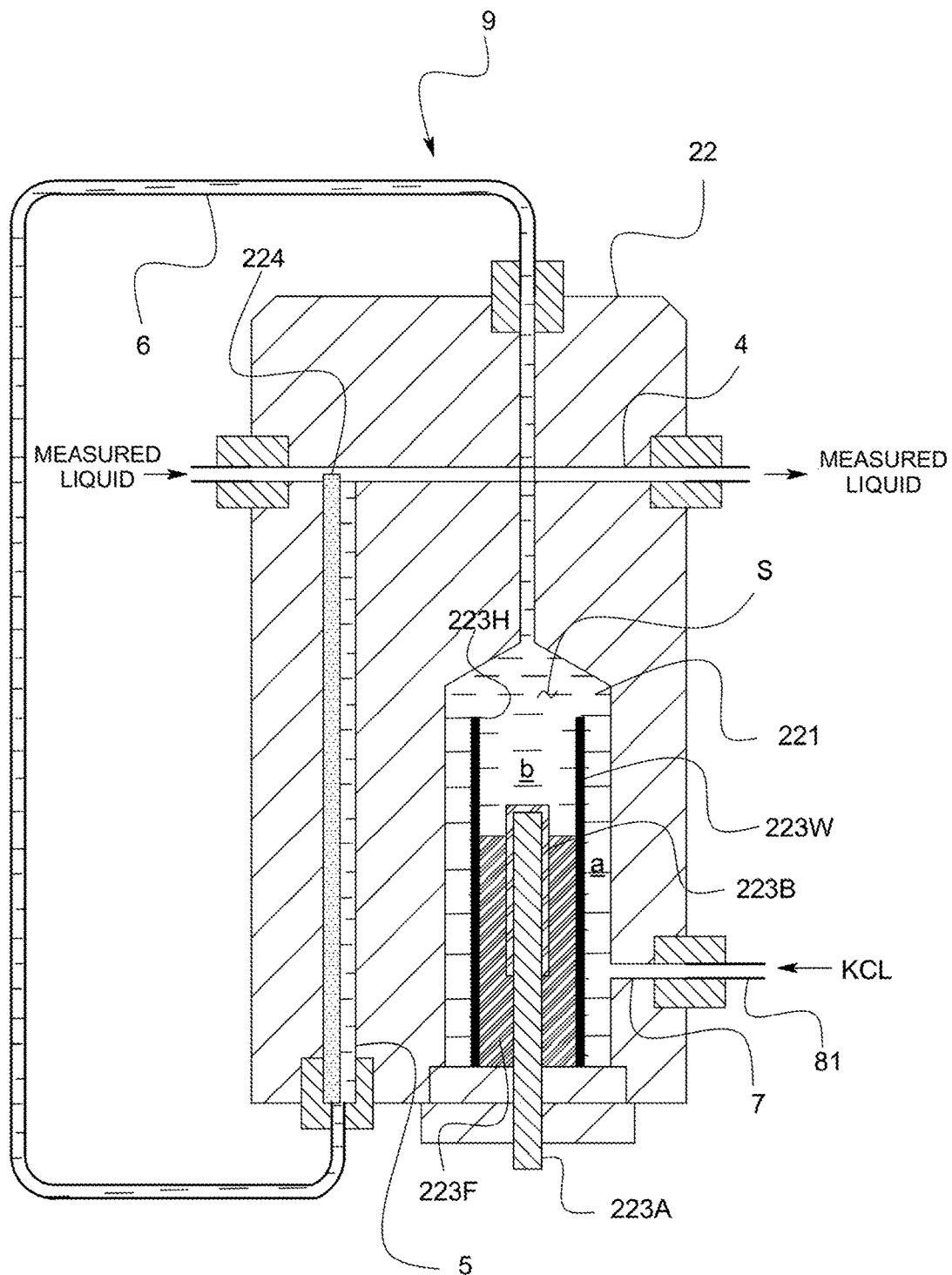
FIG. 2 is a cross-sectional view of a reference electrode according to the present embodiment.

As illustrated in FIG. 2, the reference electrode 22 is one including; a second body 222 as a casing adapted to store a second internal solution 221 inside; a second internal electrode 223 adapted to be immersed in the second internal solution 221 and output a reference potential; and a liquid junction part 224.

The second body 222 is one that is formed of a material such as PVC (polyvinyl chloride), PP (polypropylene), PVDF (polyvinylidene fluoride), PTFE (polytetrafluoroethylene), or PFA (Perfluoroalkoxy alkane) and forms a hollow block body shape. In addition, in a second internal space S as an internal space of the second body 222, the second internal solution 221 is filled. The second internal solution 221 is, for example, an aqueous solution of potassium chloride, ammonium nitrate, lithium acetate.

In the second body 222, in addition to the second internal space S, a first internal flow path 4 through which the measured liquid is introduced is provided. The first internal flow path 4 is a through-hole penetrating from one side surface to the other side surface of the second body 222, and the start edge of the first internal flow path 4 is communicatively connected to the end edge of the tubular body 213. This configuration allows the measured liquid to be introduced into the first internal flow path 4 after passing through the tubular body 213. Note that the first internal flow path 4 is one that forms a capillary shape and is very thin similarly to the tubular body 213.

Connecting parts of the main flow path, the sampling flow path 11, the tubular body, and the first internal flow path 4 are respectively sealed with a sealing member or the like, and the insides of the sampling flow path 11, the tubular body, and the first internal flow path 4 are in a state of being constantly filled with the sample or the other liquid such as a calibration liquid or a cleaning liquid.

The second internal electrode 223 is, for example, a columnar one formed of silver/silver chloride. Also, the internal electrode 223 is attached so as to penetrate through the bottom wall of the second body 222 and rise in the second internal space S, and thereby adapted to be immersed in the second internal solution 221.

The second internal electrode 223 is one including, for example, a thin rod-shaped core material 223A made of silver, and a layer 223B that covers part of the surface of the core material 223A and is made of silver chloride. Also, the second internal electrode 223 is one that is manufactured by immersing the part of the core material 223A of which the length is minimized to the extent of being able to fulfill a function as the internal electrode in, for example, dissolved or melted silver chloride for formation, and then performing a thermal treatment called annealing.

Provided around the second internal electrode 223 is a surrounding wall 223 W that rises from a place of the bottom wall of the second body 222 displaced from the second internal electrode 223 so as to surround the side circumferential surface of the second internal electrode 223 and is formed in a cylindrical shape exceeding the fore end of the second internal electrode 223 immersed in the second internal solution 221.

The surrounding wall 223W is formed of a material, for example, PVC (polyvinyl chloride), PP (polypropylene), PVDF (polyvinylidene fluoride), PTFE (polytetrafluoroethylene), PFA (Perfluoroalkoxy alkane), or epoxy resin, and a fore end surface of the surrounding wall 223W on a side opposite to a base end part closely contacting with the second body 222 is opened to form a circular opening part 22311.

The space formed between the side circumferential surface of the second internal electrode 223 and the inner circumferential surface of the surrounding wall 223W is filled with a filling material 223F such as an epoxy-based adhesive.

The filling material 223F is a material for protecting the second internal electrode 223, and filled up to a height from which the fore end of the second internal electrode 223 slightly projects.

Specifically, the possible filling height of the filling material 223F is lower than the fore end of the core material 223A, the same as the height of the fore end of the core material 223A, or between the fore end of the core material 223A and the fore end of the layer 223B made of silver chloride.

The second internal space S is divided by the surrounding wall 223W into two regions, i.e., an outside region a that is a space outside the surrounding wall 223W and an inside region b in which the second internal electrode 223 is contained, and the outside region a and the inside region b contact with each other through the opening part 223H.

The outside region a is a region outside the inside region b surrounded by the surrounding wall 223W, and the upper space is also included in the outside region a.

The liquid junction part 224 is formed in a position where the first internal flow path 4 contacts with a second internal flow path 5 that is formed separately from the second internal space S and the first internal flow path 4 in the second body 222 and externally bored such that an end part thereof reaches the first internal flow path 4.

Specifically, the second internal space S is connected to the second internal flow path 5 through an internal solution bypass flow path 6 that has the inside diameter formed to be small on the upper side of a region where the second internal electrode 223 is inserted in the view, i.e., in an end part on a side opposite to the bottom wall and separates the liquid junction part 224 and the second internal space S from each other by a predetermined distance in a part where the fore end of the small diameter part is opened toward the outside of the second body 222. Inside the second internal flow path 5, a plate-like porous member is arranged, and the liquid junction part 224 is formed such that the second internal solution 221 in the second internal flow path 5 contacts with the first internal flow path 4 through the porous member.

Meanwhile, the second internal solution 221 is reduced in amount by outflow from the liquid junction part 224 or evaporation of moisture, and therefore it is configured to provide the reference electrode 22 with an internal solution refilling mechanism 8 and allow the internal solution refilling mechanism 8 to refill the second internal solution 221 into the second internal pace S from an inlet port 7 that is bored from outside the second body 222 and thereby opened toward the outside region a, i.e., opened in the inner circumferential surface of the second body 222 facing to the outer circumferential surface of the surrounding wall 223W.

The inlet port 7 is opened toward the space between the outer circumferential surface of the surrounding wall 223W and the inner circumferential surface of the second body 222, i.e., opened on the lower side than the opening part 223H in FIG. 2, and thereby it is configured to prevent the second internal solution 222 refilled from the inlet port 7 from directly flowing into the inside region b from the opening part 223H.

The inlet port 7 may be opened not only in the side circumferential surface of the second body 222 in the second internal space S but also in the bottom surface of the second body 222 in the second internal space S.

The internal solution refilling mechanism 8 is one that as illustrated in FIG. 1, includes an internal solution refilling flow path 81, an internal solution circulation mechanism 82 adapted to control the flow of the internal solution, and an internal solution storage tank 83 adapted to store the internal solution.

The internal solution refilling flow path 81 is one that forms an internal solution flow path 9 together with the internal solution bypass flow path 6 and the second internal flow path 5, and connects between the inlet port 7 and the internal solution stored in the internal solution storage tank 83.

The internal solution circulation mechanism 82 is one that includes: an internal solution refilling pump 82P provided in the internal solution refilling flow path 81; and an internal solution control part.

In the present embodiment, the internal solution control part is such that the CPU and its peripheral devices cooperate in accordance with a predetermined program stored in the memory of the information processing circuit 3 and thereby the information processing circuit 3 fulfills a function as the internal solution control part.

The internal solution control part is configured to, for example, on the basis of an operating state of the sampling pump, determine which of a measurement state of measuring the sample, a calibration state of calibrating a measured value using the calibration liquid, and a waiting state of waiting the sample measurement or the calibration the measuring instrument 100 is in.

In addition, it is configured to, when the internal solution refilling pump 82P operates in accordance with a command signal from the internal solution control part, feed the internal solution from the internal solution storage tank 83 into the second internal space S through the internal solution refilling flow path 81 for refilling.

Connecting parts of each of the flow path and the space from the internal solution storage tank 83 to the liquid junction part 224 through the second internal space S and the internal solution flow path 9 are sealed and closed with a sealing member or the like, and the fore end of a tube forming the internal solution refilling flow path 81 is immersed in the internal solution in the internal solution storage tank 83. As a result, the flow path and space from the internal solution storage tank 83 to the liquid junction part 224 are filled with the second internal solution 221.

Note that the inlet port 7 and the internal solution refilling mechanism 8 are ones that when filling the reference electrode 22 with the second internal solution 221 from a state where the second internal solution 221 is absent as well as when refilling the internal solution, feeds the second internal solution 221 to the second internal space S for filling.

As illustrated in FIG. 1, the pH calculation part is one adapted to measure the potential difference between the first internal electrode 214 and the second internal electrode 223, and on the basis of the potential difference, calculate the pH of the measured liquid. In the present embodiment, the CPU and its peripheral devices cooperate in accordance with a predetermined program stored in the memory of the information processing circuit 3, and thereby the information processing circuit 3 fulfills a function as the pH calculation part.

Next, an example of actions of the measuring instrument 100 configured as described above will be briefly described.

When filling the internal solution using the internal solution refilling mechanism 8, the internal solution control part instructs the internal solution refilling pump 82P to refill the second internal solution 221 in the outside region a of the second internal space S from the internal solution storage tank 83 through the internal solution refilling flow path 81 and the inlet port 7.

When the second internal solution 221 having fed into the outside region a reaches the opening part 223H of the surrounding wall 223W, the second internal solution 221 flows into the inside region b from the opening part 223H. After that, the second internal solution 221 is further fed and the outside region a and the inside region b are wholly filled with the second internal solution 221. As a result, the second internal solution 221 is filled in the second internal space S.

The excess portion of the second internal solution 221 filled in the second internal space S as described fills the second internal flow path 5 through the internal solution bypass flow path 6, and flows out from the liquid junction part 224.

When refilling the internal solution using the internal solution refilling mechanism 8, the internal solution control part first determines which of the measurement state, calibration state, and waiting state the measuring instrument 100 is in, and then instructs the internal solution refilling pump 82P to refill the second internal solution 221 in the outside region a of the second internal space S at a refilling frequency and in an refilling amount appropriate for each of the states from the internal solution storage tank 83 through the internal solution refilling flow path 81 and the inlet port 7.

When the second internal solution 221 is refilled in the outside region a of the second internal space S as described, the second internal solution 221 filling the outside region a flows to the internal solution bypass flow path 6 and the second internal flow path 5 while hardly circulating with the second internal solution 221 in the inside region b surrounded by the surrounding wall 223W, and reaches the liquid junction part 224. At this time, an excess internal solution flows out from the liquid junction part 224 to the sampling flow path 11.

The refilling frequency and refilling amount of the second internal solution 221 refilled using the internal solution refilling mechanism 8 in the measurement state or the calibration state are such that the second internal solution 221 is refilled, for example, at a frequency of once per hour and by 50 µl each.

Also, the refilling frequency and refilling amount of the second internal solution 221 in the waiting state are, for example, a frequency of once per day and 50 µl each.

In the reference electrode 22 configured as described, since the surrounding wall 223W is provided around the second internal electrode 223, the second internal solution 221 in the inside region b can be suppressed from flowing and being replaced with the second internal solution 221 newly refilled, and therefore an error in a measured value occurring when the second internal solution 221 is refilled can be suppressed.

Also, by providing the inlet port 7 used to refill the internal solution between the outer circumferential surface of the surrounding wall 223W and the inner surface of the second body and on the lower side than the opening part 223H of the surrounding wall 223W in FIG. 2, it takes time for the second internal solution 221 refilled from the inlet port 7 to get over the surrounding wall 223W and flow into the inside region b. Accordingly, the internal solution can be suppressed from newly and immediately flowing into the inside region b from the opening part 223H, and therefore the second internal solution 221 around the internal electrode 223 can be effectively suppressed from flowing. As a result, the error in a measured value occurring when filling the second internal solution 221 can be more effectively suppressed.

Since the silver chloride layer 223B of the second internal electrode 223 is formed by immersing the core material 223A into dissolved or melted silver chloride, and further subjected to the thermal treatment, such as the occurrence of cracks can be suppressed to suppress the elution of silver ions from the core material 223A into the second internal solution 221 in the inside region b.

Since by making the length of the core material 223A short, and filling the space formed between the side circumferential surface of the second internal electrode 223 and the inner circumferential surface of the surrounding wall 223W with the filling material 223F such that the fore end of the second internal electrode 223 slightly projects, the second internal electrode 223 can be protected to suppress silver ions from being eluted into the second internal solution 221, the error in a measured value occurring when filling the internal solution can be further suppressed.

Since by making the silver core material 223A of the second internal electrode 223 short, the inside region b can be kept wide in the longitudinal direction of the surrounding wall 223W, and the second internal solution 221 around the internal electrode 223 can be effectively suppressed from flowing, the error in a measured value occurring when filling the second internal solution 221 can be suppressed.

Note that the present invention is not limited to the above-described embodiment.

The shape of the surrounding wall is not limited to the cylindrical shape but may be a polygonal tubular shape or an irregular tubular shape as long as the surrounding wall is one surrounding the side circumferential surface of the second internal electrode. Also, the shape of the opening part is not limited to the same shape as the cross-sectional shape of the base end part of the surrounding wall, but may be deformed in the middle of the tube, or made wider or narrower radially than the base end part.

The inlet port is not limited to one formed between the outer circumferential surface of the surrounding wall and the inner surface of the second body, but only required to be provided outside the surrounding wall.

The second internal electrode is not limited to the cylindrical one, but may be a columnar one of which the radial cross section is of a polygonal shape or an irregular shape, or a plate-shaped one.

The silver chloride layer of the second internal electrode may be formed by immersing the core material in dissolved or melted silver chloride once or multiple times.

The silver chloride layer of the second internal electrode may be formed by migration electrodeposition on the core material, an evaporation method, or a plating method, or formed using a mold or the like.

Also, the thermal treatment does not have to be performed, or may be performed at another temperature.

The silver chloride layer is not limited to one made of only silver chloride but may contain, for example, silver sulfate or the like.

The reference electrode may be one that is used to measure, such as redox potential, ion concentration, or conductivity, without limitation to pH.

The reference electrode can be applied to other various fields without limitation to a semiconductor manufacturing process.

Besides, the present invention is not limited to any of the illustrated embodiments but can be variously modified without departing from the scope thereof.

LIST OF REFERENCE CHARACTERS

Reference electrode 22
Surrounding wall 223W
Inlet port 7
Internal solution refilling mechanism 8

The invention claimed is:

1. A reference electrode comprising:
a casing adapted to store an internal solution in an internal space; and an internal electrode that rises from a bottom surface of the internal space and is arranged so as to be immersed in the internal solution, the reference electrode further comprising:
a surrounding wall that rises from the bottom surface of the internal space and of which a fore end surface is opened and a height is higher than a height of the internal electrode, wherein the surrounding wall has a tubular shape and contains the internal electrode inside so as to surround a side circumferential surface of the internal electrode; and
an inlet port provided in the casing and opened toward a space between an outer circumferential surface of the surrounding wall and an inner surface of the casing, the inlet port being for filling the internal solution.

2. The reference electrode according to claim 1, comprising:
an internal solution refilling mechanism
including a refilling pump, configured to continuously or intermittently refill the internal solution during sample measurement.

3. The reference electrode according to claim 1, wherein the internal electrode is a silver/silver chloride electrode with silver as a core material and silver chloride coated around the core material,
the reference electrode further comprising a filling material that is filled in a space formed between the side circumferential surface of the internal electrode and an inner circumferential surface of the surrounding wall.

* * * * *